(12) United States Patent
Chu et al.

(10) Patent No.: US 8,360,065 B2
(45) Date of Patent: Jan. 29, 2013

(54) OCCLUSION OF FALLOPIAN TUBES IN A VERTEBRATE SUBJECT

(75) Inventors: Michael S. H. Chu, Brookline, MA (US); Jianmin Li, Lexington, MA (US); Hamid Davoudi, Westwood, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 216 days.

(21) Appl. No.: 12/782,958

(22) Filed: May 19, 2010

(65) Prior Publication Data

US 2010/0294282 A1    Nov. 25, 2010

Related U.S. Application Data

(60) Provisional application No. 61/180,270, filed on May 21, 2009.

(51) Int. Cl.
| | |
|---|---|
| *A61F 6/06* | (2006.01) |
| *A61F 13/00* | (2006.01) |
| *A61B 19/00* | (2006.01) |
| *A61M 1/00* | (2006.01) |
| *A61M 5/178* | (2006.01) |
| *A61M 29/00* | (2006.01) |

(52) U.S. Cl. ........ 128/831; 128/830; 128/832; 128/833; 128/839; 604/28; 604/36; 604/108; 604/158; 424/422; 424/430

(58) Field of Classification Search .......... 128/830–841; 604/28, 32, 36, 38, 53, 108, 158, 213; 623/1; 424/422, 430

See application file for complete search history.

(56) References Cited

U.S. PATENT DOCUMENTS

| | | | |
|---|---|---|---|
| 6,302,108 B1 * | 10/2001 | Levine | 128/830 |
| 6,432,116 B1 * | 8/2002 | Callister et al. | 606/157 |
| 2005/0187561 A1 | 8/2005 | Lee-Sepsick et al. | |
| 2005/0217680 A1 | 10/2005 | Callister et al. | |
| 2007/0056591 A1 | 3/2007 | McSwain | |
| 2007/0282160 A1 | 12/2007 | Sheu et al. | |
| 2007/0286892 A1 | 12/2007 | Herzberg et al. | |
| 2008/0154256 A1 | 6/2008 | Payne et al. | |
| 2008/0178891 A1 | 7/2008 | McGuckin | |
| 2008/0302368 A1 | 12/2008 | McGuckin, Jr. et al. | |

* cited by examiner

*Primary Examiner* — Michael Brown
*Assistant Examiner* — Brandon L Jackson
(74) *Attorney, Agent, or Firm* — Mayer & Williams PC; David B. Bonham; Keum J. Park

(57) ABSTRACT

According to one claim of the invention, a method for occluding a fallopian tube in a vertebrate subject is described, which comprises comprising transcervically delivering a solid blocking material into the fallopian tube. In various embodiments, a fluid sealing material is delivered along with the solid blocking material. Other claims of the invention pertain to articles of manufacture, delivery devices and kits for use in occluding the fallopian tubes of a vertebrate subject.

32 Claims, 9 Drawing Sheets

OCCLUSION OF FALLOPIAN TUBES IN A VERTEBRATE SUBJECT

RELATED APPLICATIONS

This application claims priority from U.S. provisional application 61/180,270, filed May 21, 2009, which is incorporated by reference herein in its entirety.

FIELD OF THE INVENTION

The present invention relates, among other things, to methods, articles of manufacture, devices and kits for use in occluding fallopian tubes in a vertebrate subject.

BACKGROUND INFORMATION

Tubal ligation is a common method for the prevention of unwanted pregnancy. For example, a commonly used method is to tie off or clamp the fallopian tube under laparoscopy or mini-laparoscopy surgical procedures. Another approach is to tie each fallopian tube in two locations and cut the intermediate section. Other methods of ligation are electrodesiccation of the tubes to achieve ligation. There are risks of injury, scarring, cost, and recovery time associated with such surgical procedures.

Fallopian tubal ligation also can be achieved through hysteroscopic procedures. Essure microinserts are made of nitinol wrapped with dacron and are used to block the fallopian tubes once tissue in-growth completely blocks the fallopian tube. This hysteroscopic method is not effective immediately and a follow up confirmatory test after three months is required to ensure fallopian tubes are completely blocked. In the meantime alternative birth control is required. Other procedures involve the injection of various compositions within each of the fallopian tubes to block the tubes. In still other techniques, radiofrequency energy is used to thermally damage the fallopian tube, causing scarring, which occludes the tube.

SUMMARY OF THE INVENTION

According to one aspect of the invention, a method for occluding a fallopian tube in a vertebrate subject is described, which comprises transcervically delivering a solid blocking material (e.g., an open solid blocking material, for instance, a filamentous blocking material such as a mesh, suture coil, etc.) into the fallopian tube. In various embodiments, a fluid sealing material is delivered along with the solid blocking material.

Other aspects of the invention pertain to articles of manufacture, delivery devices and kits for use in occluding the fallopian tubes of a vertebrate subject.

Advantages of the present inventions include the fact that fallopian tube of a subject may be occluded with a composition that blocks sperm movement and promotes tissue in-growth such that a permanent occlusion is ultimately formed.

These and other aspects, embodiments and advantages of the present invention will become readily apparent to those of ordinary skill in the art upon review of the Detailed Description to follow.

DETAILED DESCRIPTION

The present invention relates, among other things, to methods, devices, articles of manufacture and kits for use in permanently occluding fallopian tubes in a vertebrate subject, more preferably a mammalian subject, and even more preferably a human subject, with a solid blocking material. (A typical human fallopian tube measures approximately 10 cm long and 0.7 cm in diameter.)

In one aspect of the invention, an open blocking material, more particularly, a filamentous blocking material, is employed as the solid blocking material and inserted into a fallopian tube of a subject via transcervical access using an elongated device which includes delivery chamber from which the filamentous blocking material can be released.

Figure 1A:
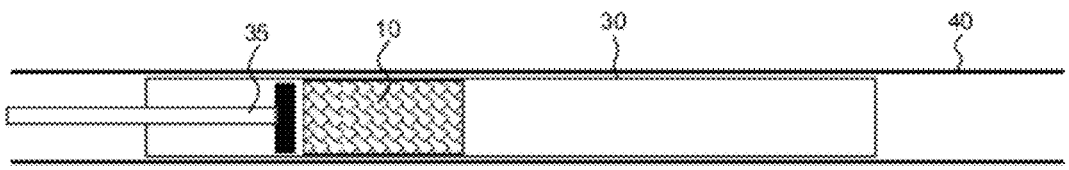
FIGS. 1A-1D are schematic illustrations showing methods for introducing into a fallopian tube a solid blocking material or a solid blocking material in combination with a fluid sealing material, in accordance with an embodiment of the invention.

Referring now to FIG. 1A, in accordance with one aspect of the invention, an assembly is shown which includes an elongated device with a delivery channel 30 and a solid blocking material 10. The delivery channel 30 may be, for example, a working channel of any commercially available hysteroscope, or it may be the lumen of a catheter delivery tube, among other options. Inside the delivery channel 30 is provided a plunger 35, which can be used to advance the blocking material 10 out of the delivery channel 30 and into a fallopian tube 40 of a subject.

The blocking material is inserted into the fallopian tube of a subject to occlude the fallopian tube. The blocking material may be made, for example, of any suitable biocompatible material, which can be implanted permanently. It is preferably stable in both chemically and in mechanical dimension, so that it keeps the fallopian tube sealed permanently. The material also preferably promotes rapid scar tissue formation, with the blocking material being used as a scaffold for tissue in-growth, which results in permanent occlusion of the fallopian tube. Thus, it is preferred for such a blocking material to have numerous spaces (e.g., pores) to promote quick and permanent scar tissue formation.

For example, in some embodiments, the blocking material may comprise randomly coiled threads (e.g., metallic or polymeric treads) or one or more threads pre-formed into a 3-dimensional shape, for example, a shape of circular, oval or annular cross-section (e.g., a ball, cylinder, etc.).

In other embodiments, the blocking material may comprise a fabric, preferably a mesh (e.g., a polymeric or metallic mesh). Meshes in accordance with the present invention include woven meshes and non-woven meshes (including knitted meshes, felt meshes and spunbound meshes, among others). Meshes in accordance with the present invention preferably have inter-filament spaces (pores) that typically range in width from 0.01 mm to 5 mm (e.g., 0.01 mm to 0.1 mm to 0.5 mm to 1 mm to 3 mm to 5 mm), more typically 0.5 to 3 mm.

Mesh widths and lengths for the practice of the invention can vary widely. However, for sheet-like meshes of relatively similar length and width (e.g., circular, polygonal, etc.), typical widths vary from 1 to 100 mm (e.g., 1 to 2 to 5 to 10 to 20 to 50 to 75 to 100 mm), more typically 10 to 20 mm, while for elongated sheet-like meshes (e.g., rectangular strips, etc.), typical widths vary from 2 to 20 mm (e.g., 2 to 3 to 5 to 8 to 10 to 15 to 20 mm) and typical lengths vary from 20 to 60 mm (e.g., 20 to 30 to 40 to 50 to 60 mm), more typically 30 to 50 mm, among other possibilities.

Meshes in accordance with the present invention preferably have filaments that range in diameter from 0.025 to 0.625 mm (0.025 to 0.05 to 0.10 to 0.25 to 0.50 to 0.625 mm), more typically 0.05 to 0.25 mm. Filaments for forming meshes in accordance with the present invention are preferably polymeric filaments which remain intact in vivo (i.e., biostable polymeric filaments), and include those formed from (a) polyolefins, including homopolymers and copolymers of C1-C8 alkenes, for example, polypropylene, (b) fluoropolymers, including homopolymers and copolymers of C1-C8 alkenes in which one or more hydrogen atoms are substituted with fluorine, for example, polytetrafluoroethylene and polyvinylidene fluoride, and (c) biostable polyesters, including, for example, polyethylene terephthalate, among various other polymers.

In certain embodiments, the blocking material is rendered radiopaque (e.g., by including metallic particles in the material, by metal plating the material, etc.) to facilitate location confirmation and follow up.

Moreover, in various embodiments, it is desirable for the blocking material (e.g., threads, meshes, etc.) to have sharp edges which are able to cut and/or penetrate the inner lumen of the fallopian tube, thereby increasing the resistance between the blocking material and the fallopian tube wall (i.e., anchoring the blocking material) while also stimulating scar tissue formation.

For example, where a mesh is used as a blocking material it may be tanged to anchor the mesh against the inner surface of the fallopian tube and promote scarring. Tangs are the strands of fibers that are exposed on the edge of a mesh and are created when a mesh is cut. In some embodiments, a portion of a mesh may be de-tanged to allow it to be repositioned within the fallopian tube. In other embodiments the entire mesh may be de-tanged. Such a de-tanged mesh would have the option of being removed or repositioned before tissue in-growth. The mesh may need to be removed due to infection or other complications.

In some embodiments, the blocking material may be oriented or compacted by the delivery device during implantation to totally occlude the bodily tube. In some embodiments, the mesh is preformed by prepackaging the mesh in a delivery device, for example, in a particular orientation. In some embodiments, the blocking material is preformed in a particular stand-alone shape.

Where preformed in a device or in a particular stand-alone shape, the blocking material may be comprise one or more of the following materials among others: one or more randomly coiled threads, one or more randomly bunched meshes, one or more meshes formed into a specially folded configuration, one or more threads and/or meshes formed into a three-dimensional shape of circular, oval or annular cross-section (e.g., a preformed sphere, oblate spheroid, prolate spheroid, cylinder, annulus, etc.), and so forth.

Figure 1B:
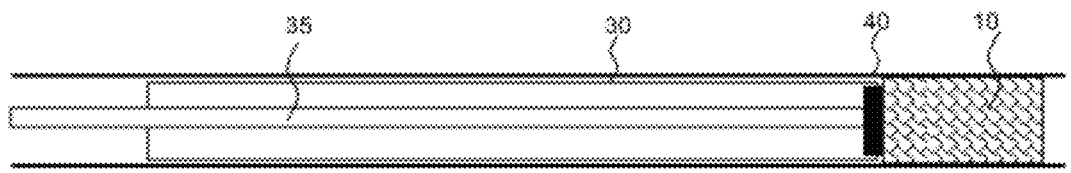

For example, referring now to FIG. 1A, an embodiment is shown in which a blocking material 10 is pre-loaded into a delivery channel 30 of a delivery device. During delivery, the end of the delivery channel 30 is advanced to a predetermined fallopian tube location 40 as schematically shown in FIG. 1A. Once at this location, the plunger 35 is advanced within the delivery channel 30, pushing the blocking material 10 from the delivery channel 30 as shown in FIG. 1B. In the embodiment shown, the blocking material 10 is a resilient material which is compressed in the delivery channel 30 and expands to engage the internal surface of the fallopian tube 40 upon emerging from the delivery channel 30. The delivery channel 30 and plunger 35 are then withdrawn, leaving the blocking material 10 in the fallopian tube 40. As elsewhere herein, the procedure can then be repeated on the contralateral side to occlude both fallopian tubes.

In certain embodiments, a sealing material is delivered prior to, along with and/or after the blocking material. The sealing material is a fluid material, for example, a gel or a biodegradable adhesive material (e.g., curable composition that is flexible upon cure) which acts to block sperm and egg movement immediately upon implantation while at the same time allowing tissue growth (e.g., permanent scar tissue) into the spaces associated with the blocking material over a short period of time. After delivery of the blocking material and sealing material, the sealing material may be positioned, for example, in one or more of the following locations: (a) within the spaces (e.g., pores) associated with the open (e.g., filamentous) blocking material, (b) within the fallopian tube at a position distal to (i.e., on the ovary side of) the blocking material, and (c) within the fallopian tube at a position proximal to (i.e., on the uterus side of) the blocking material. In certain of these embodiments, the mesh acts as scaffolding for the fluid sealing material. For example, the mesh may prevent the fluid sealing material from migrating.

Figure 1C:
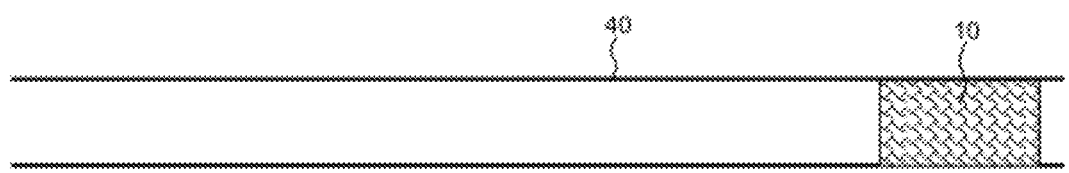
Figure 1D:
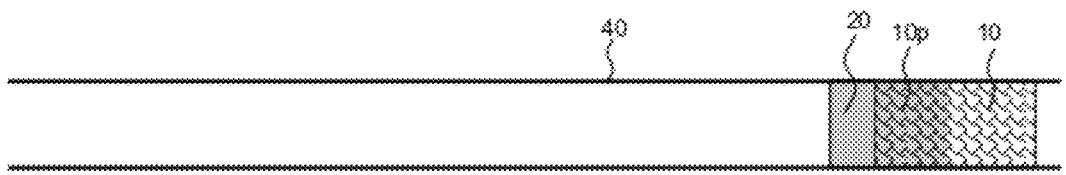

For example, after the sealing material 10 has been placed in the fallopian tube 40 as shown in FIG. 1C, if desired, a device (e.g., a catheter) may be inserted into the fallopian tube to deliver an amount of sealing material 20 as shown in FIG. 1D. The subsequently injected sealing material 20 may penetrate all of the sealing material 10 or a portion of the sealing material 10p as shown.

Figure 2A:
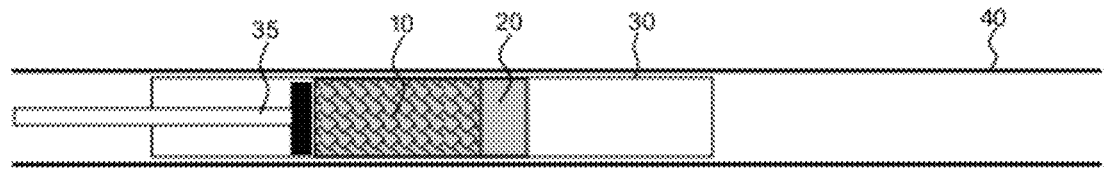
FIGS. 2A-2D are schematic illustrations showing methods for introducing into a fallopian tube a solid blocking material in combination with a fluid sealing material, in accordance with an embodiment of the invention.
Figure 2B:
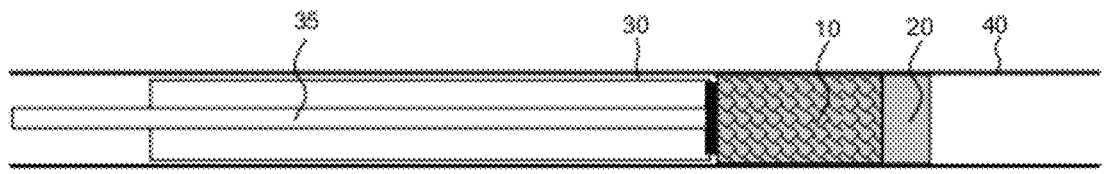
Figure 2C:
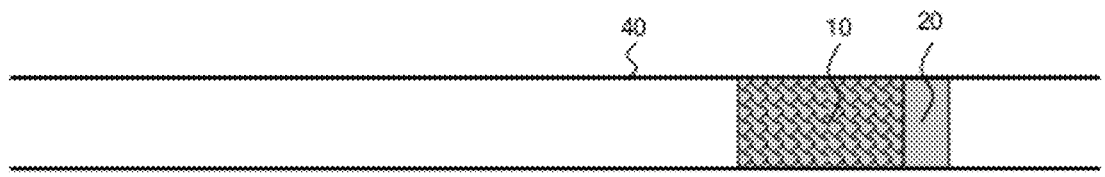
Figure 2D:
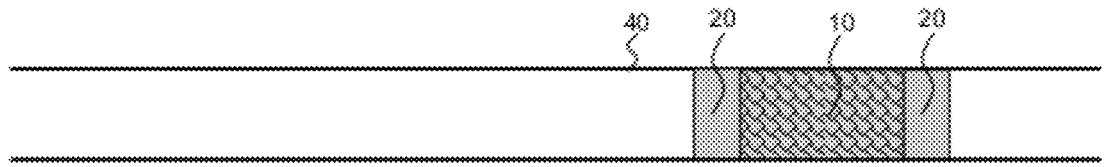

In another embodiment shown in FIG. 2A, a sealing material 20 and blocking material 10 (whose spaces are partially or completely filled with sealing material) are pre-loaded into a delivery channel 30 of a delivery device. During delivery, the end of the delivery channel 30 is advanced to a predetermined fallopian tube location 40 as shown in FIG. 2A. Once at this location, the plunger 35 is advanced within the delivery channel 30, pushing the blocking material 10 and sealing material 20 from the delivery channel 30 as shown in FIG. 2B. The delivery channel 30 and plunger 35 are then withdrawn, leaving the blocking material 10 and sealing material 20 in the fallopian tube 40 as shown in FIG. 2C. If desired, an additional device (e.g., a catheter) may be inserted into the fallopian tube (e.g., via a deliver channel 30) to deliver an additional amount of sealing material 20 as shown in FIG. 2D.

As noted above, the sealing material is a fluid material, for example, a gel or a biodegradable adhesive material which acts to block sperm movement, while at the same time allowing tissue growth into the blocking material. Preferably the sealing material is removed from the site (e.g., bioeroded, biodisintegrated, biodegraded, etc.), for example, at least 50% of the material (e.g., 50% to 75% to 90% to 95% to 100%) is removed from the site over a period of 1 to 2 to 4 weeks.

Examples of sealing materials (e.g., gels, adhesives, etc.) may be selected, for example, from one or more of the following, among others: collagen, elastin, thrombin, fibronectin, gelatin, gelatin-thrombin mixtures, gelatin-resorcinol-formaldehyde-glutaraldehye (GRFG) glue, fibrin, fibrin glue, albumin and glutaraldehyde tissue adhesive, tropoelastin, gell-forming peptides including self-assembling peptide hydrogels, Ethibloc amino acid gel, laminin, proteoglycans, glycosaminoglycans, glycoproteins, fibrin glue, activated platelet gel, atelocollagen, starch, pectin, cellulose, alkyl cellulose, e.g. methylcellulose, hydroxyalkyl cellulose, alkylhydroxyalkyl cellulose, cellulose sulfate, carboxymethyl cellulose, carboxyethyl cellulose, chitin, carboxymethyl chitin, hyaluronic acid, alginic acid, agar, agarose, glycogen, dextran, dextran sulfate, carboxymethyl dextran, curdlan, pectin, pullulan, xanthan, chondroitin, chondroitin sulfate, carboxymethyl chitosan, chitosan, dermatan sulfate, keratan sulfate, carrageenan, starch, amylose, amylopectin, poly-N-glucosamine, polymannuronic acid, polyglucuronic acid, polyguluronic acid, poly(alkylene oxides) such as poly(ethylene oxide), polypropylene oxide), poly(ethylene oxide-co-propylene oxide), poly(vinyl alcohol), ethylene vinyl alcohol copolymer, polyethylene glycol-based materials (e.g., FOCAL SEAL from Focal, Inc. and COSEAL from Cohesion Technologies, Inc.), monostearoyl glycerol co-succinate/polyethylene glycol (MGSA/PEG) copolymers, as well as salt forms and crosslinked forms of the foregoing.

In certain embodiments, a two-component curable adhesive composition is employed as the sealant material. In these embodiments, it is preferred that the curing kinetics are sufficiently slow to allow the two components to be mixed, at which time the mixture can be delivered prior to, along with and/or after the blocking material as described above. For example, two liquid components may be mixed by mixing screw during injection. The liquids combine/interact when channeled through the threads of the mixing screw.

In some embodiments, the sealing material is provided with a spermicide to enhance the effectiveness of the material. Examples of spermicides include benzalkonium chloride, chlorhexidine digluconate, D-propranolol HCl, muhric acid, menfegol, nonoxynol-9, and octoxynol-9.

In certain embodiments, the sealing material is a commercially available spermicidal gel. Commercially available gels (which contain nonoxynol-9) include the following: ADVANTAGE 24 gel (Lake Consumer), CONCEPTROL gel (Advanced Care), GYNOL jelly (Advanced Care), GYNOL II ES jelly (Advanced Care), KOROMEX jelly (Quality Health), KOROMEX CRYSTAL CLEAR gel (Quality Health), ORTHO-GYNOL jelly (Advanced Care), SHUR-SEAL jelly (Milex Products), VCF gel (Apothecus Pharmaceutical).

In some embodiments, the sealing material is provided with an agent to promote tissue in-growth. Examples of such agents include proinflammatory agents and/or sclerosing agents.

Proinflammatory agents can be selected, for example, from suitable endotoxins, cytokines, chemokines, prostaglandins, lipid mediators, and other mitogens. Specific examples of proinflammatory agents from which suitable agents can be selected include the following: growth factors such as platelet derived growth factor (PDGF), fibroblast growth factor (FGF), transforming growth factor (such as TGF-alpha and TGF-beta), epidermal growth factor (EGF), insulinlike growth factor (IGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), superoxide, hydrogen peroxide, zymosan, bacterial lipopolysaccharide, imiquimod, various pharmaceutically acceptable salts and derivates of the foregoing, and combinations of the foregoing, among other agents.

Suitable sclerosing agents for the practice of the invention can be selected, for example, from the following: inorganic materials such as aluminum hydroxide, sodium hydroxide, silver nitrate and sodium chloride, as well as organic compounds, including alcohols such as ethanol, acetic acid, trifluoroacetic acid, formaldehyde, dextrose, polyethylene glycol ethers (e.g., polidocanol, also known as laureth 9, polyethylene glycol (9) monododecyl ether, and hydroxy-polyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyanoactyalte and methyl 2-cyanoacrylate, ethanolamine, ethanolamine oleate, bacterial preparations (e.g., corynebacterium and streptococcal preparations such as picibanil) and mixtures of the same, among others.

In certain embodiments, the invention is directed to elongated devices which include a delivery chamber from which a filamentous blocking material can be released, for example, the delivery chamber of such a device may comprise a preloaded composition comprising (a) a blocking material such as that described above, for instance, a filament or a collection of filaments (including a mesh) that is preloaded in a particular shape, for example, in a shape of cylindrical, oval or annular cross-section (e.g., a filamentous ball, filamentous cylinder, etc.) and, optionally, (b) a fluid sealing material such as that described above (e.g., tissue adhesive, gel, etc.).

In certain embodiments, the invention is directed to a kit that comprises (a) a blocking material, for example, a filament or a collection of filaments (including a mesh) that is preformed in a particular shape, for example, in a shape of cylindrical, oval or annular cross-section, among others, or a collection of filaments (including a mesh) that can be formed into a particular shape by the user, for example, in a shape of cylindrical, oval or annular cross-section, either ex vivo (e.g., in the delivery chamber of a device) or in vivo (e.g., in the fallopian tube), (b) a fluid sealing material (e.g., tissue adhesive, gel, etc.) and (c) optionally, a delivery device (e.g., a catheter, a scope with a working channel, etc.) which is configured to deliver the blocking material and the fluid sealing material to the fallopian tube via a transcervical route.

Various particular mesh designs will now be discussed. In some embodiments, the mesh is provided with a molded tip and/or suture.

In addition, several additional delivery devices and various placement techniques will be described, by which one or more meshes can be delivered in numerous orientations, including random and organized orientations (e.g., the mesh may be simply be laid in place, folded, bunched, twisted, etc.). A single piece of mesh may be placed or more than one piece of mesh can be placed. Multiple meshes can be placed in parallel or in series.

In some embodiments, the delivery device may incorporate a hysteroscope for viewing. In other embodiments, a hysteroscope may be provided within a lumen of the delivery device or used alongside of the delivery device for viewing. In others embodiments the delivery device is configured to incorporate a guidewire. In still other embodiments, the delivery device is radiopaque such that is can be delivered with a fluoroscope, in which case the mesh may also be radiopaque. In some embodiments, the device comprises a rigid elongated shaft. In other embodiments, the device comprises a flexible elongated shaft.

In each of the embodiments to follow, a fluid sealing material (e.g., tissue adhesive, gel, etc.) may be delivered to the subject before, along with and/or after the delivery of the mesh to the subject.

In various embodiments of the invention, a rectangular mesh is employed. A schematic perspective view of such a mesh 110 is shown in FIG. 3. For example, the mesh may have a length of 20 to 50 mm (20 to 30 to 40 to 50 mm), may have a width of 0.5 to 20 mm (e.g., 0.5 to 1 to 2 to 3 to 5 to 8 to 10 to 15 to 20 mm), and may be formed from fibers having a diameter between 0.025 to 0.625 mm (0.025 to 0.05 to 0.10 to 0.25 to 0.50 to 0.625 mm), more typically 0.05 mm to 0.25 mm, which fibers may be woven to form spaces/pores ranging from 0.01 to 5 mm (e.g., 0.01 mm to 0.1 mm to 0.5 mm to 1 mm to 3 mm to 5 mm), more typically 0.5 to 3 mm in width.

Figure 6:

The mesh may be formed from a single layer of material or multiple layers. In various embodiments, a single layer mesh is employed. The smaller the diameter of the fiber used to manufacture the mesh, the closer the weave that is possible, enabling the production of smaller pore sizes. It should also be understood that pore sizes can be made smaller by compaction or folding of the mesh before or during delivery. For example, a single layer mesh may be placed as shown in FIG. 6 to form multiple layers. When two or more mesh layers having the same pore size are stacked (e.g., by folding a single mesh, by stacking multiple meshes), the "through" pore size is effectively reduced because no two layers of mesh will have pores that line up perfectly with each other.

In certain embodiments, a long piece of mesh may be provided to allow the user to cut the mesh to any desired length and/or to provide multiple mesh units when cut.

When a mesh of this type is cut, tangs are produced during the cutting process, leaving exposed pointed fibers extending from the edges. Tangs can be removed by a heating process to melt the extended fibers down to a fiber crossover point in a process known as de-tanging. De-tanging melts and joins the fibers together and prevents the mesh from un-raveling. De-tanged portions of the mesh can be manipulated without tangs penetrating into surrounding tissue.

Figure 3A:
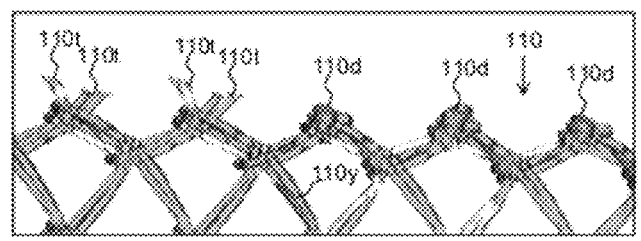
FIG. 3A is a detail of an edge portion of a rectangular knotted mesh, showing tanged and de-tanged areas, in accordance with an embodiment of the invention.
Figure 3:
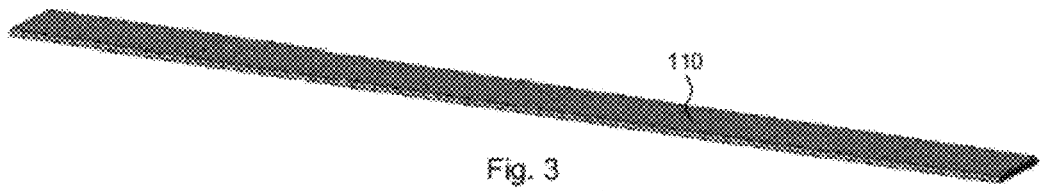
FIG. 3 is a schematic perspective view of a rectangular mesh material, in accordance with an embodiment of the invention.

FIG. 3A is a detail of an edge portion of a mesh 110 that is formed from a knotted multifilament yarn 110y. The mesh 110 has been cut from a larger mesh material, leaving tangs 100t, which are shown at two of the knots at the edge of the mesh. Three of the knots shown at the edge of the mesh have been de-tanged 110d by heating the tangs to above their melting point.

Other types of meshes can be molded, extruded, knitted or stamped. Tangs can be produced by cutting the mesh. Secondary operations can be used to cut off, melt or even laser off tangs, if desired.

Figure 4:
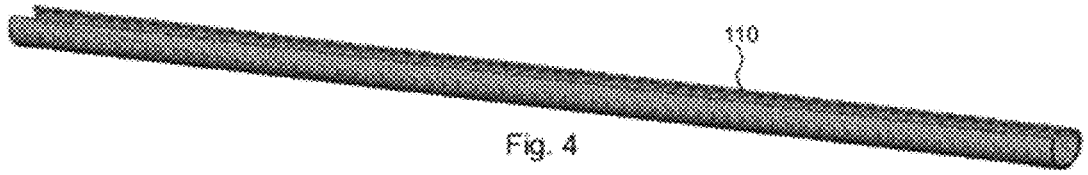
FIGS. 4-8 are schematic perspective views illustrating various ways in which a rectangular mesh like that of FIG. 3 can be oriented, in accordance with various embodiments of the invention.

FIG. 4 illustrates the mesh 110 of FIG. 3 wrapped in a semicircular arrangement. Such a shape may be created, for example, by wrapping the mesh 110 around the inner tube 102 of a delivery device 100 (partial perspective view) like that shown in FIG. 9. The outer tube 104, which acts as a sheath 104 in FIG. 9, covers the mesh 110 and its associated tangs 110t (at its edges) entirely during delivery, to prevent inadvertent engagement of the mesh 110 with adjacent tissue. When the sheath 104 is pulled back (arrow A) the exposed portion of the mesh 110 will tend to spring back to a flat state like that shown in FIG. 3. The exposed tangs will engage surrounding tissue as the mesh 110 is released from the delivery device to secure the mesh 110 in place.

Figure 5:
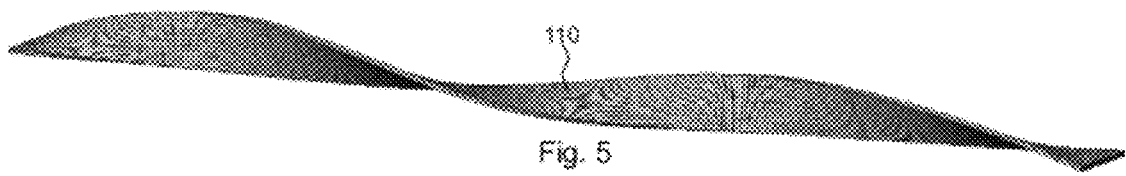
Figure 9:
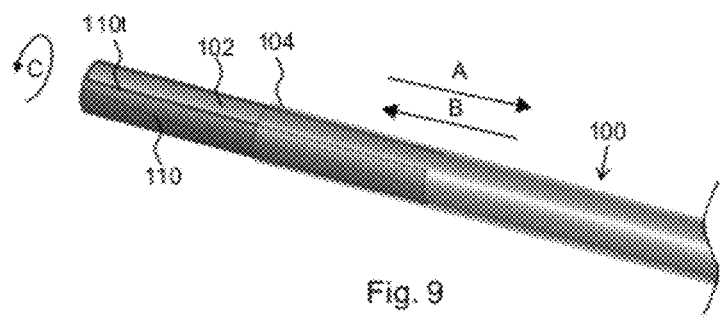
FIG. 9 is a schematic perspective view of the distal end of the delivery device of FIG. 10A, upon partial retraction of the sheath of the delivery device, in accordance with an embodiment of the invention.
Figure 18:
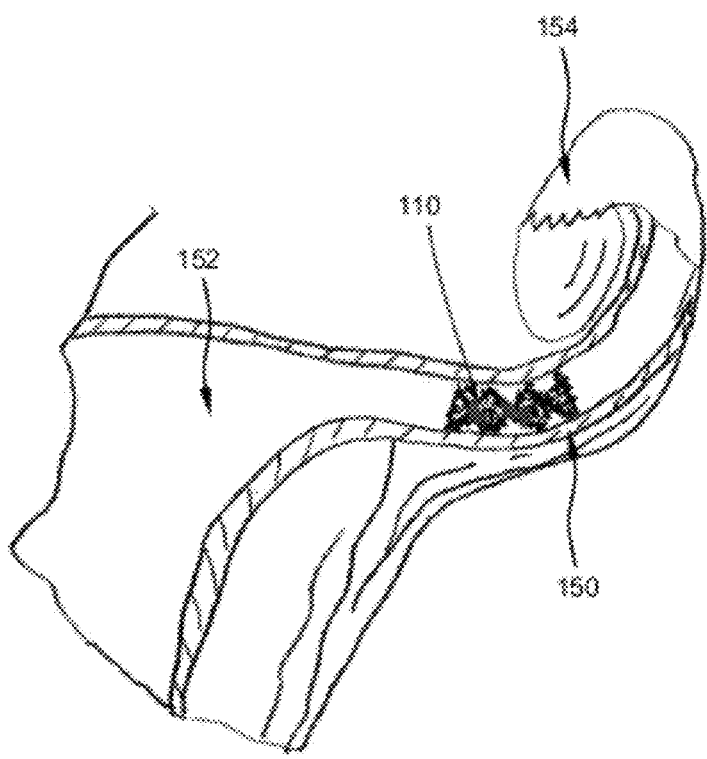
FIGS. 18-20 are schematic illustrations showing how meshes can be placed in a fallopian tube of a patient in various specific orientations, in accordance with various embodiment of the invention.

FIG. 5 illustrates the mesh 110 of FIG. 3 in a twisted or spiral orientation. As the mesh 110 of FIG. 9 is released from the delivery device 100, a portion of exposed tangs will engage tissue as noted above. The mesh 110 may then be twisted by rotating the sheath 104 or rotating the entire delivery device 100 as shown by arrow C in FIG. 9. The cross-sectional area or occlusion area of the twisted mesh is increased relative to the mesh in the absence of twisting. Continual twisting will further shorten the length of the strip and compact the mesh in a spiral. See FIG. 18 for a schematic illustration of a twisted mesh 110 positioned in the fallopian tube 150. Also shown in FIG. 18 are the uterus 152 and ovary 154 of the subject.

It should be understood that in certain cases, the mesh may have a very small width (less than 0.7 mm wide). The mesh length can be displaced in a spiral configuration, spiraling from the outside diameter towards the center to occupy the fallopian tube's entire inner diameter, thereby occlude the fallopian tube. Conversely, such a mesh may be randomly placed/packed into the fallopian tube. In this case the mesh length may be much longer than the preferred upper range of 50 mm described above.

Figure 20:
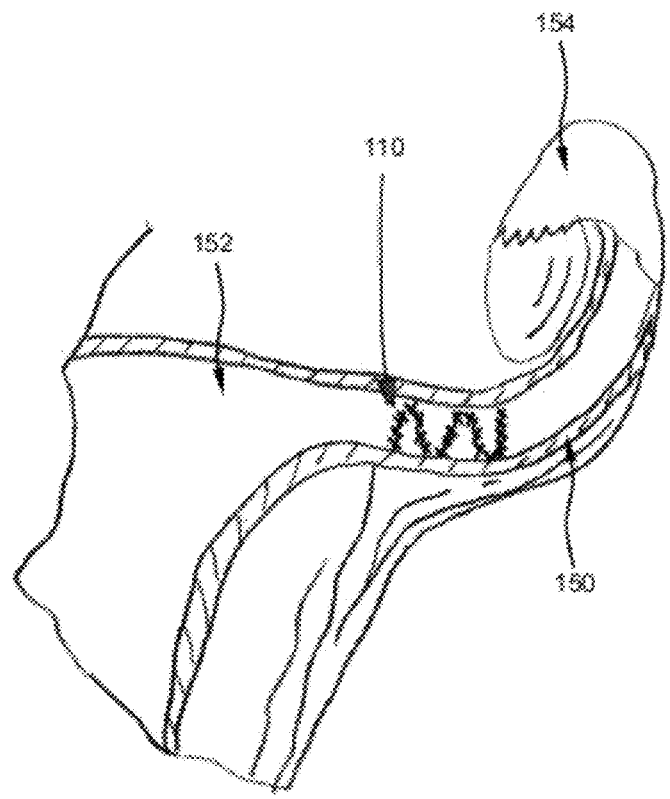

FIG. 6 illustrates a mesh 110 like that of FIG. 3, in a bunched or accordion-type orientation. An orientation of this type may be formed in vivo as follows: As the sheath 104 is drawn back from the delivery device 110 of FIG. 9, that portion of the mesh with exposed tangs 110e will engage adjacent tissue. The sheath 104 of the delivery device 100 can be reciprocated along arrows A and B, causing the mesh 110 to bunch in vivo. The cross-sectional area or occlusion area of the mesh 110 is increased prior to that which would be achieved without bunching. Further bunching will further shorten the length of the mesh 110. See FIG. 20 for a schematic illustration of a bunched mesh 110 positioned in the fallopian tube 150.

Figure 7:
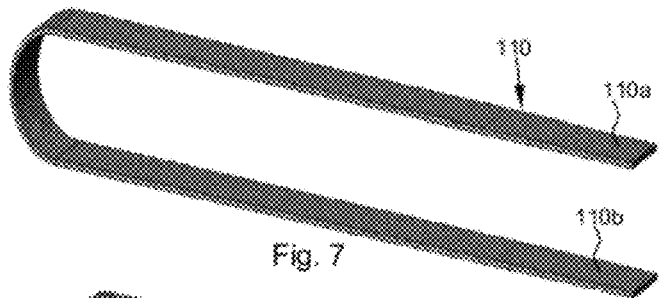
Figure 19:
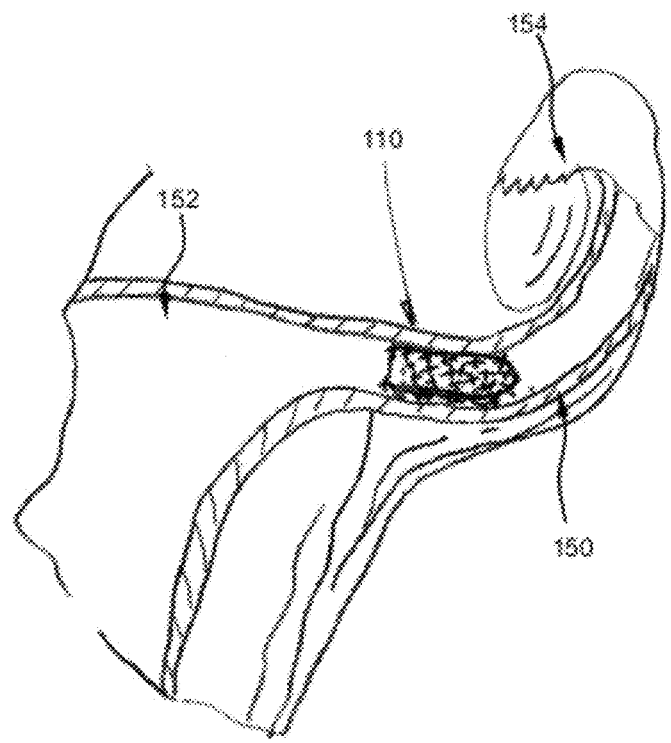

FIG. 7 illustrates the mesh 110 like that of FIG. 1, which has been folded over, thus doubling the mass per length and also doubling the number of tangs per length, even without twisting or bunching. This configuration has two mesh legs 110a, 110b. A mesh 110 in the configuration of FIG. 7 can also be delivered by a delivery device 100 like that shown in FIG. 9. It should be understood that both legs 110a, 110b of the mesh 110 of FIG. 7 can also be twisted or bunched using the delivery device of FIG. 9. See FIG. 19 for an illustration of a mesh 110 positioned in the fallopian tube 150 of a patient. In this embodiment, a guide wire can be passed through the pores/openings of the mesh 110 and/or a scope can be passed through the openings of the mesh 110 to facilitate device guidance.

Figure 8:
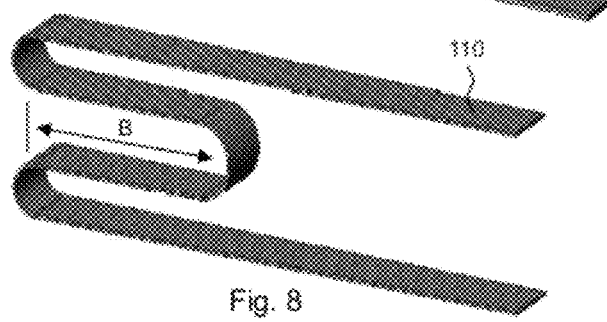
Figure 21:
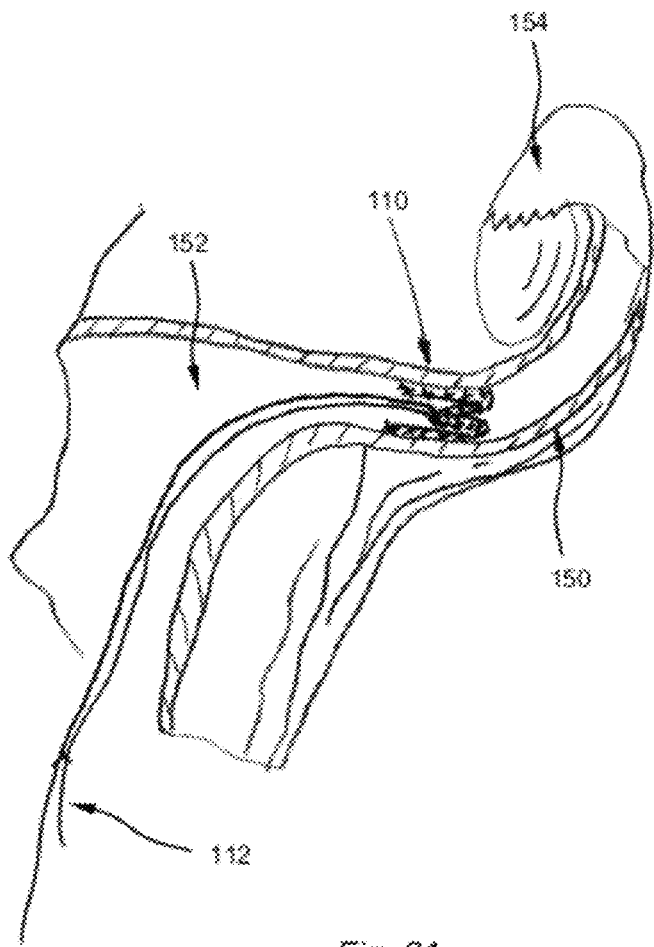
FIG. 21 is a schematic illustration showing the placement of a mesh and suture loop in a fallopian tube of a patient, in accordance with an embodiment of the invention.

FIG. 8 illustrates the mesh 110 of FIG. 3 folded over to a thickness of 4 times, thus quadrupling the mass per length and also quadrupling the number of tangs per length. A loop suture is used to invert the mesh of FIG. 7 to that of FIG. 8. The legs of FIG. 8 can also be twisted or bunched. See FIG. 21 for an illustration of the mesh of FIG. 8 positioned in a fallopian tube 150 of a patient. The suture 112 in FIG. 21, which is used to invert the mesh from a shape like that of FIG. 7 to a shape like that of FIG. 8, has not yet been removed.

Figure 10A:
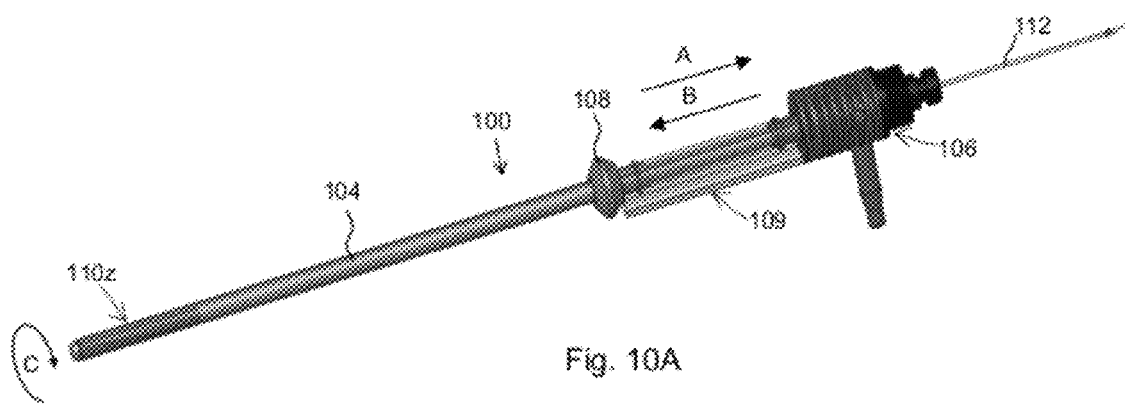
FIG. 10A is a schematic perspective view of a delivery device, in accordance with an embodiment of the invention.

FIG. 10 is a schematic perspective view of the entire delivery device 100 of FIG. 9. FIG. 11 illustrates the delivery device of FIG. 10 with a view of the disassembled components. The delivery device 100 comprises a sheath 104 and a hub 108 having a first ring 103a. The delivery device 100 also comprises an inner tube 102 with a fitting 106 (which acts as a handle) attached at its proximal end 102p. A lumen extends along the entire length of the inner tube 102 and the fitting 106. The lumen can be sized for a guidewire only or for a hysteroscope (which would configuration would also accommodate a guidewire). The fitting may provide a second ring 103b. The fitting 106 may also provide two ports 107b, 107a. The back port 107b may be used, for example, for the insertion of a device such as a guidewire, scope, and/or suture. The additional port 107a can be used, for example, for irrigation, inflation, suction, injection, drainage or other procedure. A lumen also extends along the entire length of the sheath 104 and hub 108. The lumen of the sheath 104 is sized to house a mesh assembly 110z as it is seated on the outer surface of the inner tube 102. A spacer 109 is provided to maintain the sheath 104 in a stationary position (in both axial directions) during introduction of the delivery device 100 through the cervix by means of two grooves 109g which snap onto the ring 103a of the hub 108 and ring 103b of the fitting 106. When the spacer is removed the sheath 104 and inner tube 102 can slide axially relative to each other.

Figure 10B:
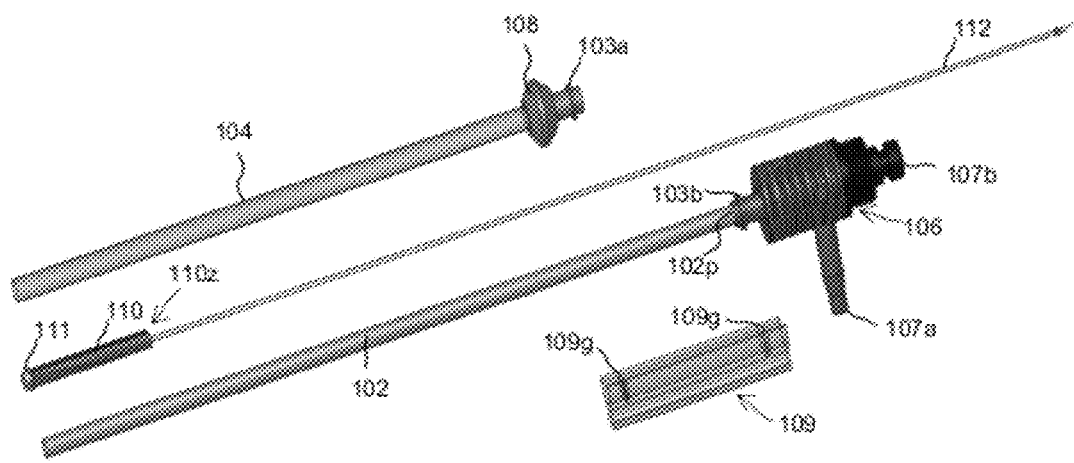
FIG. 10B is a view of the delivery device of FIG. 10A upon disassembly, in accordance with an embodiment of the invention.
Figure 11:
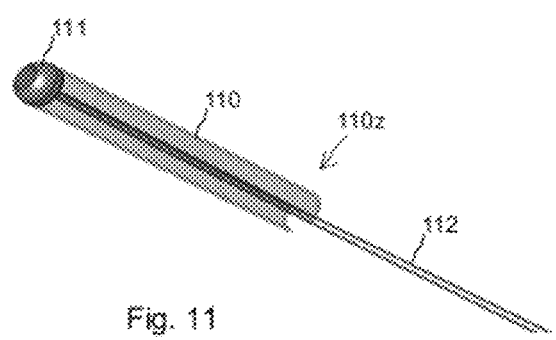
FIG. 11 is a schematic perspective view of a mesh, in accordance with an embodiment of the invention.

The mesh assembly 110z illustrated in FIG. 10B, which is shown enlarged in FIG. 11, is somewhat different than the mesh shown in FIG. 7. In addition to a mesh 110, the mesh assembly 110z illustrated in FIG. 10B and FIG. 11 also includes an insert molded tip 111 and a looped suture 112 threaded through the mesh. The tip 111 provides ease of insertion and has a through lumen to provide scope and/or guide wire access. The tip 111 can be barbed to help maintain and anchor it within the fallopian tube. As with the mesh 110, the tip 111 may also be formed from a biostable polymer such as polypropylene. The suture 112 loop provides the ability to position the mesh from an orientation like that of FIG. 7 to an orientation like that of FIG. 8, in which case the tip 112 should not be barbed to allow the end of the assembly to be pulled back. The suture 112 is preferred to be looped such that it can be easily removed from a position external to the body. The suture 112 loop can be cut external to the body and one end of the suture pulled to un-loop the suture 112 from the mesh 110 or mold tip 111. In some embodiments, the suture 112 can be used to retrieve the mesh 110, if inadvertently placed or used for temporary placement.

In some embodiments the suture 112 can be used to maintain the mesh 110 on the OD of the inner tube 102 and no sheath 104 is needed, for example, by attaching a suture to each end of the legs and holding the suture in tension external to the tube. In some embodiments, a suture 112 is not used.

Figure 12:
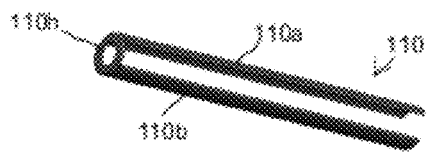
FIG. 12 is a schematic perspective view of a mesh, in accordance with another embodiment of the invention.

In some embodiments, a tip 111 is not used. In this regard, FIG. 12 illustrates a mesh 110 like that of FIG. 7, which has been modified by cutting a hole 110h and thermosetting in a mold to create to the shape illustrated. The mesh 110 can be thermoset in the mold to have additional surface area, such as bumps or dimples. Two mesh legs 110a, 110b are shown, which can be longer or shorter than the length shown. Other embodiment may have less or more than two mesh legs. In this embodiment a looped suture is not employed, although in other embodiments a looped suture may be employed, analogous to that shown in FIG. 11.

Figure 13:
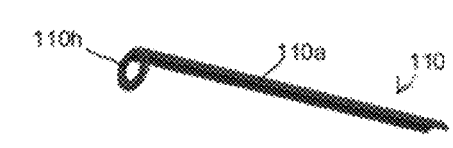
FIG. 13 is a schematic perspective view of a mesh assembly, in accordance with an embodiment of the invention.

FIG. 13 illustrates a mesh 110 like that of FIG. 12 with only a single mesh leg 110a. The leg 110a can be longer or shorter than shown. A suture can also be looped into the mesh, analogous to that shown in FIG. 11.

Other modifications are also possible. For example, slits may be cut into the mesh leg(s) to create more tangs to engage tissue (not shown).

The components of the delivery device 100 shown in FIGS. 10A and 10B can be assembled by the user or the manufacturer. For example, the suture 112 (when present) of the mesh assembly 110z may be threaded through the lumen of the inner tube 102 and out the device port 107b of the fitting 106. The mesh 110 of the mesh assembly 110z is positioned on the OD and at the front end of the inner tube 102. The sheath 104 is slid over the mesh 110 and inner tube 102 to "sandwich" the mesh 110 between the sheath 104 and inner tube 102. The spacer 109 is snapped onto the hub ring 103a and fitting ring 103b to secure the sheath 104 in place.

The delivery device 100 of FIG. 10A can be advanced with that aid of a hysteroscope (not shown) inserted through the lumen of the inner tube 102 and along the side of the suture. The hysteroscope will provide visualization to pass the device through the cervix and into the fallopian tube. (If the fallopian tube has already has been accessed by a guide wire, the delivery device can be slid over the guide wire for placement.)

Figure 17:
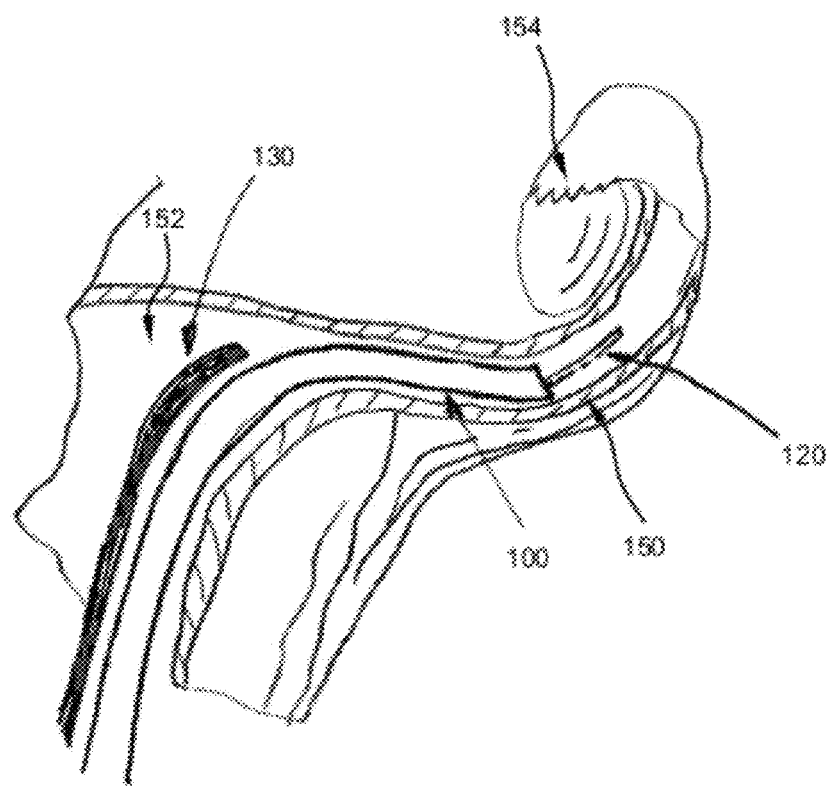
FIG. 17 is a schematic illustration of a system for placement of one or more meshes in a fallopian tube of a patient, in accordance with an embodiment of the invention.

In another embodiment, the delivery device 100 is advanced over a guidewire 120 and the scope 130 is used alongside the delivery device 100 for viewing as shown in FIG. 17.

Once the delivery device 100 is positioned in the fallopian tube 150, to deploy the mesh 110, the spacer 109 is removed, and the sheath 104 is moved vis-à-vis the inner tube 102. With reference to FIG. 10A, the user has several options or combinations of options for placement of the mesh, which may include the following options, among others: To expose a part or the entire length of mesh 110, the sheath 104 is pulled by the hub towards the fitting 106 (in the direction of arrow A). Once a portion of the tangs engage the fallopian tube: (a) the sheath 104 (or the entire device 100) can be rotated (in the direction of arrow C) to twist or spiral a portion of the mesh 110 as it is deployed, (b) a suture can be pulled (in the direction of arrow A) to convert the mesh from a orientation like that of FIG. 7 to a orientation like that of FIG. 8, in which case a length of B (see FIG. 8) of the mesh 110 may be de-tanged to allow the mesh 110 to slide when pulled, or (c) the sheath 104 can be retracted (in the direction of arrow A) then advanced forward (in the direction of arrow B) to bunch the mesh 110 to a orientation like that of FIG. 6. To complete the deployment of the mesh 110, after the sheath is fully withdrawn (in the direction of arrow A), the distal end of the inner tube 102 is then retracted (in the direction of arrow A) back into the sheath 104.

In another method for delivery, referring again to FIG. 10A, the spacer 109 is first removed. Then, the sheath 104 is held stationary while the inner tube 102 is retracted (in the direction of arrow A) beyond the mesh 110. A marking on the inner tube (not shown) can indicate the desired extent of retraction. To deploy the mesh, the inner tube 102 is then advanced forward (in the direction of arrow B) to push out and bunch the mesh 110. If preferred, the inner tube 102 can also be rotated to twist the mesh 110. The mesh 110 can also be deployed by fully retracting the sheath (in the direction of arrow A) to deposit the mesh, followed by retraction of the entire device 100.

In one embodiment of the delivery method, the mesh (and thus the associated tangs) is reciprocated to cause injury to the fallopian tube, thereby spurring in-growth of tissue into the mesh to anchor and totally occlude the lumen.

In another embodiment a brush (not shown) is used to cause uniform injury to the fallopian tube before the mesh is placed (e.g., by advancing and retracting the brush one or more times within the fallopian tube). In some instances, mesh is not placed after the use of the brush, with the fallopian tissue healing and closing within hours or days as a result of the injury.

It is apparent from the above that there are multiple methods, including combinations of methods, for deploying a mesh using a delivery device like that describe in FIG. 10A to achieve various orientations for the mesh, including combinations of orientations for the mesh.

Figure 14A:
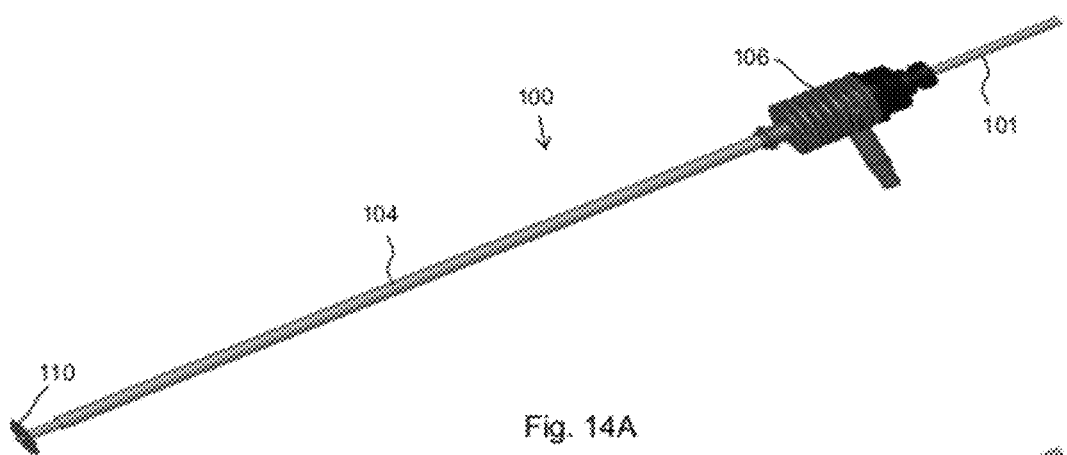
FIG. 14A is a schematic perspective view of a delivery device, in accordance with an embodiment of the invention.
Figure 14B:
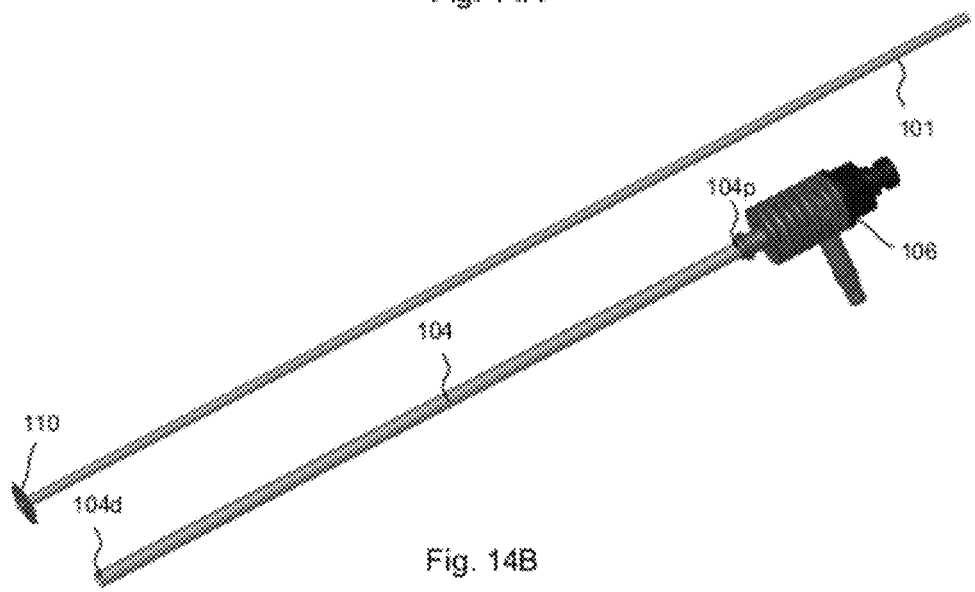
FIG. 14B is a view of the delivery device of FIG. 14A upon disassembly, in accordance with an embodiment of the invention.
Figure 15A:
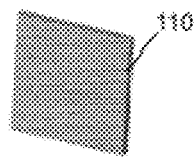
FIGS. 15A-15H are schematic perspective views of various sheet-like mesh designs, in accordance with various embodiments of the invention.
Figure 15B:
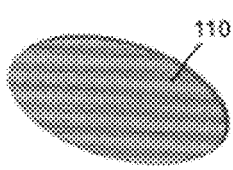
Figure 15C:
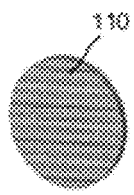
Figure 15D:
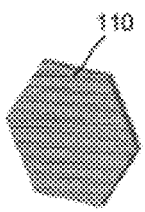
Figure 15E:
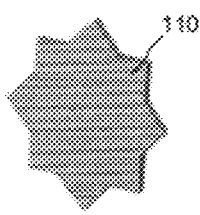
Figure 15F:
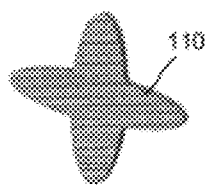
Figure 15G:
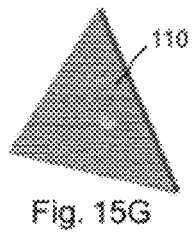
Figure 15H:
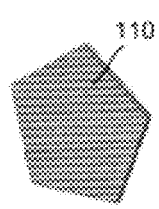

FIG. 14A is another embodiment of a delivery device 100 in accordance with the invention. FIG. 14B is a disassembled view of FIG. 14A. The delivery device 100 comprises a pusher 101 and a sheath 104 with a fitting 106 attached at its proximal end 104p. The lumen of the sheath 104 is sized to accept a hysteroscope (not shown) and to accommodate the pusher 101 when the scope is removed. The sheath 104 may be placed visually with a hysteroscope inserted in its lumen for placement through the cervix and into the fallopian tube, among other placement techniques (see above). Once the sheath 104 is positioned, the scope can be removed. A mesh 110 can be transported through the lumen of the sheath 104 with use of the pusher 101. A single mesh 110 or more than one mesh 110 can be secured (e.g., skewered) at the tip of the pusher 101 and inserted into the lumen of the sheath 104. If desired, a sealing material (e.g., gel, adhesive, etc.) may be inserted into the lumen 104 prior to or along with the mesh 110. For instance, the mesh 110 may be loaded with sealing material (e.g., by dipping the mesh in sealing material) and inserted into the lumen 104. The mesh 110 folds to conform to the width of the sheath 104 lumen and recovers some of its width once it exits the distal tip 104d of the sheath 104. The tangs of the mesh 110 can engage surrounding tissue to anchor the mesh 110 in place within the fallopian tube. Withdrawal of the pusher 101 will complete the deposition of the mesh within the fallopian tube. Additional 110 meshes can be deposited by reloading and advancing the pusher 101 by the user.

Meshes 110 of various shapes can be delivered with a device like that of FIGS. 14A-14B, including various circular, oval, star-shaped and polygonal shapes, such as those shown in FIGS. 15A-15H. Such meshes are typically tanged, but may be de-tanged, if desired. Some of the meshes 110 shown have sharp corners to further assist anchoring in a fallopian tube. Moreover, a variety of other mesh designs, including the meshes 110 of FIGS. 7, 11, 12, 13, among others, can be used with a delivery device like that of FIGS. 14A-14B.

The meshes of FIGS. 15A-15H are shown in a flat configuration. When secured (e.g., skewered) at the tip of the pusher 101 as shown in FIG. 14B and placed in the body, the mesh (so long as it has a diameter greater than that of the fallopian tube) becomes roughly conical in shape. In other embodiments, a cone shaped mesh having an open end (e.g., like an ice cream cone) is secured at the tip of the pusher.

It is noted that the pusher 101 may have two or more skewer posts on the distal end of the pusher such that the mesh can be twisted by the rotation of the pusher. It is also noted that the pusher of FIGS. 14A-14B and the meshes of FIGS. 15A-15H (as well as other meshes) can be used with the delivery device of FIG. 7 to place additional meshes.

Figure 22:
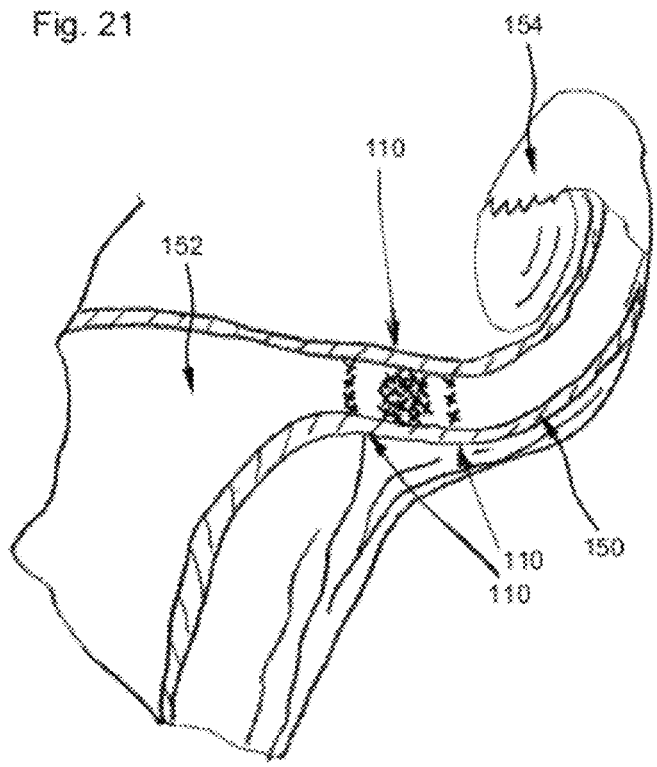
FIG. 22 is a schematic illustration showing the placement of three meshes in a fallopian tube of a patient, in accordance with an embodiment of the invention.

In some embodiments, two or more meshes are delivered, individually or at the same time. FIG. 22 illustrates the use of multiple meshes 110 to occlude the fallopian tube 150. The meshes 110 can have the same or different pore sizes as noted above. The meshes 110 can be of differing shape (planer, spherical, cylindrical, etc.) and/or of differing orientation (e.g., twisted, bunched, etc.).

Figure 16A:
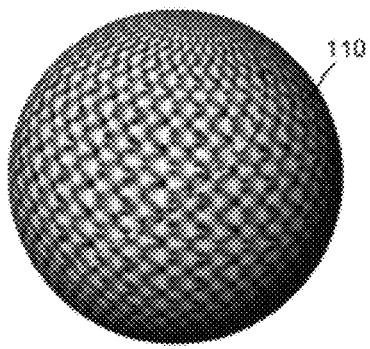
FIGS. 16A and 16B are schematic perspective views of two three-dimensional mesh configurations, in accordance with two embodiments of the invention.
Figure 16B:
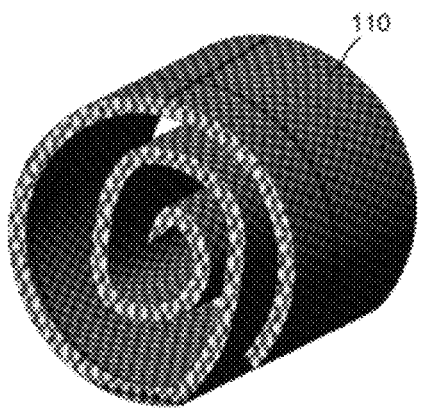

FIGS. 16A and 16B illustrate alternative mesh 110 embodiments, in which the meshes are provided in 3 dimensional shapes. The meshes 110 can be rolled or shaped into a ball shape (FIG. 16A) or coiled and provided in an overall cylindrical shape (FIG. 16B). The meshes 110 preferably comprise exposed tangs. The ball and coil shapes allow the meshes 110 to be compressed and deployed through a sheath (see sheath 104 of FIG. 14B), whereupon the meshes expand upon deployment in the fallopian tube.

As previously indicated, to enhance fallopian tube obstruction, a sealing material may be delivered prior to, along with (e.g., after saturating the mesh with the sealing material) and/or after the deposition of the meshes, in the embodiments described above.

Various aspects of the invention of the invention relating to the above are enumerated in the following paragraphs:

Aspect 1. A method for occluding a fallopian tube comprising transcervically delivering a solid blocking material and a fluid sealing material into the fallopian tube.

Aspect 2. The method of aspect 1, wherein the solid blocking material is a mesh having exposed tangs.

Aspect 3. The method of aspect 2, wherein the mesh is twisted, folded or bunched at the time of delivery to the fallopian tube.

Aspect 4. The method of aspect 2, wherein multiple meshes are delivered to the fallopian tube.

Aspect 5. The method of aspect 1, wherein the fluid sealing material is selected from a gel and a curable composition that is flexible upon cure.

Aspect 6. The method of aspect 1, wherein the fluid sealing material comprises an agent selected from a spermicide and a tissue in-growth promoter.

Aspect 7. The method of aspect 1, wherein at least 90% of the fluid sealing material removed from the fallopian tube by the body over a period of two weeks.

Aspect 8. The method of aspect 1, wherein the fluid sealing material is delivered prior to the solid blocking material, along with the solid blocking material, after the solid blocking material, or a combination of the foregoing.

Aspect 9. The method of aspect 1, wherein the mesh is saturated with the fluid sealing material at the time of delivery to the fallopian tube.

Aspect 10. A kit for occluding a fallopian tube of a subject comprising (a) a solid blocking material, (b) a fluid sealing material, and (c) a delivery device that is configured to transcervically deliver the solid blocking material and the fluid sealing material into the fallopian tube.

Aspect 11. The kit of aspect 10, wherein the solid blocking material comprises a mesh.

Aspect 12. The kit of aspect 11, wherein the mesh comprises exposed tangs.

Aspect 13. The kit of aspect 11, wherein the mesh is a substantially planar filamentous mesh.

Aspect 14. The kit of aspect 11, wherein the mesh is a substantially non-planar filamentous mesh comprising a substantially circular, oval or annular cross-section.

Aspect 15. The kit of aspect 11, wherein the mesh comprises two or more legs and a suture loop.

Aspect 16. The kit of aspect 11, wherein the delivery device is preloaded with the mesh.

Aspect 17. The kit of aspect 10, wherein the fluid sealing material is selected from a gel material and a curable composition that is flexible upon cure.

Aspect 18. The kit of aspect 10, wherein the fluid sealing material comprises a spermicide.

Aspect 19. The kit of aspect 10, wherein the fluid sealing material comprises a tissue in-growth promoter.

Aspect 20. The kit of aspect 10, wherein the delivery device is preloaded with the sealing material and a mesh.

Aspect 21. The kit of aspect 10, wherein the delivery device comprises (a) an elongated tubular member comprising a proximal end, a distal end, a lumen and a handle that comprises a port that accesses the lumen and (b) a pushing member configured to advance the solid blocking material into the port, through the elongated tubular member, and out of the distal end of the elongated tubular member.

Aspect 22. The kit of aspect 21, wherein the delivery device further comprises a scope.

Aspect 23. A mesh delivery device comprising: (a) an elongated inner tubular member comprising a proximal end, a distal end, a first lumen, and a stopping element disposed at or near its proximal end; (b) an elongated outer tubular member comprising a proximal end, a distal end and a second lumen that is sized to allow the distal end of the inner tube to be inserted into the proximal end of the outer tubular member and through the outer tubular member such that the distal end for the inner tubular member emerges from the distal end of the outer tubular member when the stopping element of the inner tubular member engages the proximal end of the outer tubular member, (c) a spacer that is configured to engage the inner and outer tubular members such that the proximal end of the outer tubular member is spaced at a fixed axial distance from the stopping element of the inner tubular member.

Aspect 24. The mesh delivery device of aspect 23, wherein the stopping element is a handle that comprises one or more ports that access the first lumen.

Aspect 25. The mesh delivery device of aspect 23, wherein the inner tubular member comprises a first engagement member, wherein the outer tubular member comprises a second engagement member, and wherein the spacer is configured to simultaneously engage the first and second engagement members.

Aspect 26. The mesh delivery device of aspect 25, wherein the first engagement member comprises a first ring, wherein the second engagement member comprises a second ring, and wherein the spacer comprises first and second grooves for receiving the first and second rings.

Aspect 27. The mesh delivery device of aspect 23, wherein the device is preloaded with the mesh and wherein the mesh is positioned between the outer and inner tubular members proximal the distal end of the device.

Aspect 28. The mesh delivery device of aspect 27, wherein the mesh comprises two or more legs and a suture loop.

Aspect 29. The mesh delivery device of aspect 27, wherein the mesh comprises two or more legs and a molded tip.

Although various embodiments are specifically illustrated and described herein, it will be appreciated that modifications and variations of the present invention are covered by the above teachings and are within the purview of the appended claims without departing from the spirit and intended scope of the invention.

What is claimed:

1. A method for occluding a fallopian tube comprising transcervically delivering a solid blocking material comprising a mesh formed from a biostable material and a fluid sealing material into the fallopian tube, wherein said fluid sealing material is removed from the fallopian tube by the body after delivery.

2. The method of claim 1, wherein the mesh has exposed tangs.

3. The method of claim 1 wherein the mesh is twisted, folded or bunched at the time of delivery to the fallopian tube.

4. The method of claim 1, wherein multiple meshes are delivered to the fallopian tube.

5. The method of claim 1, wherein the fluid sealing material is selected from a gel and a curable composition that is flexible upon cure.

6. The method of claim 1, wherein the fluid sealing material comprises an agent selected from a spermicide and a tissue in-growth promoter.

7. The method of claim 1, wherein at least 90% of the fluid sealing material removed from the fallopian tube by the body over a period of two weeks.

8. The method of claim 1, wherein the fluid sealing material is delivered prior to the solid blocking material, along with the solid blocking material, after the solid blocking material, or a combination of the foregoing.

9. The method of claim 1, wherein the mesh is saturated with the fluid sealing material at the time of delivery to the fallopian tube.

10. The method of claim 1, wherein a suture loop is threaded through the mesh during delivery of the mesh and wherein the suture loop is removed after delivery of said mesh.

11. The method of claim 1, wherein the mesh comprises polypropylene.

12. The method of claim 1, wherein at least 50% of the fluid sealing material is removed from the fallopian tube by the body over a period of four weeks.

13. A kit for occluding a fallopian tube of a subject comprising
(a) a solid blocking material comprising a biostable mesh, (b) a fluid sealing material that is removable from the fallopian tube by the body after delivery, and (c) a delivery device that is configured to transcervically deliver the solid blocking material and the fluid sealing material into the fallopian tube.

14. The kit of claim 13, comprising and a suture loop threaded through the mesh.

15. The kit of claim 13, wherein the mesh comprises exposed tangs.

16. The kit of claim 13, wherein the mesh is a substantially planar filamentous mesh.

17. The kit of claim 13, wherein the mesh is a substantially non-planar filamentous mesh comprising a substantially circular, oval or annular cross-section.

18. The kit of claim 13, wherein the mesh comprises two or more legs and a suture loop.

19. The kit of claim 13, wherein the delivery device is preloaded with the mesh.

20. The kit of claim 13, wherein the fluid sealing material is selected from a gel material and a curable composition that is flexible upon cure.

21. The kit of claim 13, wherein the fluid sealing material comprises a spermicide.

22. The kit of claim 13, wherein the fluid sealing material comprises a tissue in-growth promoter.

23. The kit of claim 13, wherein the delivery device is preloaded with the sealing material and the mesh.

24. The kit of claim 13, wherein the delivery device comprises (a) an elongated tubular member comprising a proximal end, a distal end, a lumen and a handle that comprises a port that accesses the lumen and (b) a pushing member configured to advance the solid blocking material into the port, through the elongated tubular member, and out of the distal end of the elongated tubular member.

25. The kit of claim 24, wherein the delivery device further comprises a scope.

26. A mesh delivery device comprising:
(a) an elongated inner tubular member comprising a proximal end, a distal end, a first lumen, and a stopping element disposed at or near its proximal end;

(b) an elongated outer tubular member comprising a proximal end, a distal end and a second lumen that is sized to allow the distal end of the inner tube to be inserted into the proximal end of the outer tubular member and through the outer tubular member such that the distal end for the inner tubular member emerges from the distal end of the outer tubular member when the stopping element of the inner tubular member engages the proximal end of the outer tubular member, (c) a spacer that is configured to engage the inner and outer tubular members such that the proximal end of the outer tubular member is spaced at a fixed axial distance from the stopping element of the inner tubular member during introduction of the delivery device and is configured to disengage the inner and outer tubular members such that the inner and outer tubular members are allowed to slide axially relative to one another.

27. The mesh delivery device of claim 26, wherein the stopping element is a handle that comprises one or more ports that access the first lumen.

28. The mesh delivery device of claim 26, wherein the inner tubular member comprises a first engagement member, wherein the outer tubular member comprises a second engagement member, and wherein the spacer is configured to simultaneously engage the first and second engagement members.

29. The mesh delivery device of claim 28, wherein the first engagement member comprises a first ring, wherein the second engagement member comprises a second ring, and wherein the spacer comprises first and second grooves for receiving the first and second rings.

30. The mesh delivery device of claim 26, wherein the device is preloaded with the mesh and wherein the mesh is positioned between the outer and inner tubular members proximal the distal end of the device.

31. The mesh delivery device of claim 30, wherein the mesh comprises two or more legs and a suture loop.

32. The mesh delivery device of claim 30, wherein the mesh comprises two or more legs and a molded tip.

* * * * *

UNITED STATES PATENT AND TRADEMARK OFFICE
CERTIFICATE OF CORRECTION

| | | |
|---|---|---|
| PATENT NO. | : 8,360,065 B2 | Page 1 of 1 |
| APPLICATION NO. | : 12/782958 | |
| DATED | : January 29, 2013 | |
| INVENTOR(S) | : Michael S. H. Chu, Jianmin Li and Hamid Davoudi | |

It is certified that error appears in the above-identified patent and that said Letters Patent is hereby corrected as shown below:

Specification, col. 3, lines 32-33, after "polymeric" change "treads", to --threads--

Specification, col. 5, line 60, after "poly(ethylene oxide)" change "polypropylene oxide)" to --poly(propylene oxide)--

Specification, col. 9, line 49, after "which" delete the word "would"

Specification, col. 12, line 53, after the word "invention" delete the words "of the invention"

Claims, col. 15, claim 14, line 8, after the word "comprising" delete the word "and"

Signed and Sealed this
Ninth Day of April, 2013

Teresa Stanek Rea
*Acting Director of the United States Patent and Trademark Office*